United States Patent [19]

Amano et al.

[11] Patent Number: 5,508,173
[45] Date of Patent: Apr. 16, 1996

[54] ANALYTICAL ELEMENT FOR MEASUREMENTS OF ENZYME ACTIVITY

[75] Inventors: Yoshikazu Amano; Kazuya Kawasaki; Harumi Katsuyama, all of Asaka, Japan

[73] Assignee: Fuji Photo Film Co., Ltd., Kanagawa, Japan

[21] Appl. No.: 373,885

[22] Filed: Jan. 17, 1995

Related U.S. Application Data

[63] Continuation of Ser. No. 449,486, Dec. 11, 1989, abandoned, which is a continuation of Ser. No. 914,469, Oct. 2, 1986, abandoned.

[30] Foreign Application Priority Data

Oct. 2, 1985 [JP] Japan .................................. 60-219703

[51] Int. Cl.$^6$ ................................ C12Q 1/28; C12Q 1/26; C12Q 1/52
[52] U.S. Cl. .................................. 435/28; 435/16; 435/25; 436/169; 436/170; 422/56; 422/60
[58] Field of Search ................................ 435/28, 16, 805, 435/810, 25; 436/169, 170; 422/56, 60

[56] References Cited

U.S. PATENT DOCUMENTS 4,503,145   3/1985   Katsuyama et al. ....................... 435/28
4,786,595   11/1988   Arai et al. ................................. 435/25

FOREIGN PATENT DOCUMENTS 0165588   12/1985   European Pat. Off. ..

*Primary Examiner*—Toni R. Scheiner
*Attorney, Agent, or Firm*—McAulay Fisher Nissen Goldberg & Kiel

[57] ABSTRACT

A multilayer analytical element for measuring enzyme activity in a liquid sample such as a body fluid which is less affected by intrinsic pyruvic acid contained in the liquid sample is disclosed. The analytical element comprises a support, a reagent layer, an optionally provided other layer, and a porous spreading layer. The reagent layer and/or the optionally provided other layer contain pyruvic acid oxidase. The characteristic feature of the analytical element lies in that the spreading layer has a specific void volume in the range of 3–15 μl/cm$^2$.

10 Claims, No Drawings

ANALYTICAL ELEMENT FOR MEASUREMENTS OF ENZYME ACTIVITY

The principle of the method can be illustrated by the following representative reaction formula:

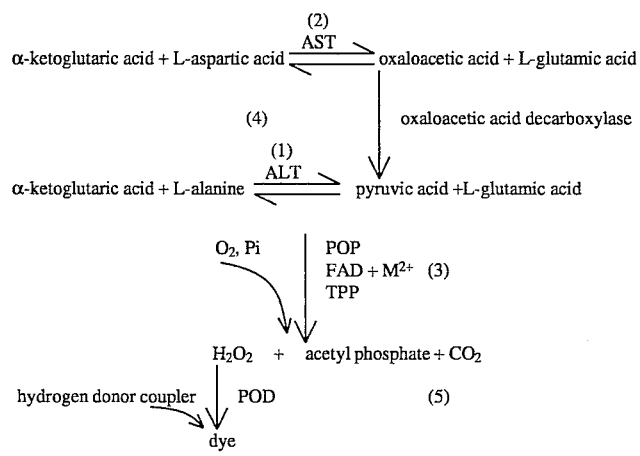

This is a continuation of application Ser. No. 07/44,486, filed Dec. 11, 1989, now abandoned, which, in turn, is a continuation of application Ser. No. 06/914,469, filed Oct. 2, 1986, now abandoned.

BACKGROUND OF THE INVENTION

1. Field of the Invention

The present invention relates to a multilayer chemical analytical element employable for determination of a specific substance contained in fluids taken from living body, such as blood. More particularly, the invention relates to a multilayer analytical film suitably employed for the measurement of transaminase activity utilizing the reaction in which pyruvic acid oxidase participates.

2. Description of Prior Art

Various kinds of transaminase are known as amino group-transferring enzymes. Particularly, as for alanine aminotransferase (ALT) and aspattic acid aminotransferase (AST), variation of the concentration thereof in blood is one criterion in finding a liver disease, so that the measurement of ALT or AST activity is very important in the diagnosis of the liver disease.

ALT and AST are enzymes for catalyzing the following reactions (1) and (2), respectively:

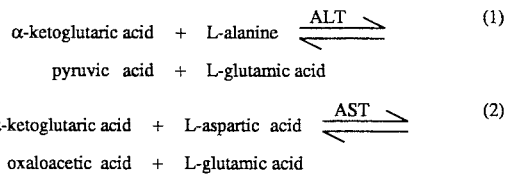

As a method for measuring the activity of various transaminases in the living body, there is known a method comprising the steps of producing pyruvic acid by reaction of the transaminase with a substrate, and subjecting the produced pyruvic acid to reaction with pyruvic acid oxidase and a peroxidase-containing color-forming indicator composition for detecting hydrogen peroxide for measuring the amount of the pyruvic acid by colorimetry to determine the transaminase activity, as described in Japanese Patent Provisional Publication No. 55(1980)-13068.

Abbreviations in the above formulae represent the following:

AST: aspartic acid aminotransferase
ALT: alanine aminotransferase;
Pi: inorganic phosphoric acid;
POP: pyruvic acid oxidase;
FAD: flavine adenine dinucleotide
TPP: thiamine pyrophosphate
$M^{2+}$: divalent metal; and
POD: peroxidase.

In more detail, pyruvic acid is produced in the reaction (1) catalyzed by ALT. Otherwise, oxaloacetic acid produced in the reaction (2) catalyzed by AST is converted by the action of oxaloacetic acid dehydrocarbon enzyme (4) to produce pyruvic acid. The pyruvic acid thus produced is converted to hydrogen peroxide according to the corresponding conjugated reaction (3) catalyzed by POP. Through the reaction in which the hydrogen peroxide serves as a substrate, a hydrogen donor and a coupler react with each other a coupling reaction (5) to give a dye. The thus produced dye is determined by colorimetry.

When the above-described determination method is used for an aqueous liquid, a complicated and time consuming series of chemical reactions in the aqueous liquid are required. Further, an interference from so-called intrinsic pyruvic acid (namely, pyruvic acid originally contained in the liquid sample) may present an even more complicated operation and longer period of time are required for the analysis in order to prevent the interference.

For coping with these difficulties in the liquid system, a so-called dry chemistry has been developed. An integral multilayer analytical element employable in the dry chemistry is described, for instance, in Japanese Patent Publication No. 53(1978)-21677 and Japanese Patent Provisional Publication No. 55(1980)-164356. A multilayer analytical element for the measurement of transaminase activity according to the dry chemistry using pyruvic acid oxidase is described in Japanese Patent Provisional Publication No. 57(1982)-144996. Recently, it is desired that the influence by various interfering substances be decreased and the analysis can be performed by a rapid and simple operation. One of the interfering substances is the intrinsic pyruvic acid.

The normal concentration of the pyruvic acid in human blood (e.g., serum, blood plasma and whole blood) generally ranges from 0.3 to 0.6 mg/dl, and the concentration sometimes reaches an abnormally high value of not lower than 2 mg/dl. The concentration of the pyruvic acid in blood increases in the case of diseases, such as, serious cirhosis of liver, liver coma or uremia. There are certain control serums having a high concentration of pyruvic acid ( e.g., not lower than 2 mg/dl ).

In the case of measuring the transaminase activity within a relatively short period of time (e.g., less than 10 minutes) using a conventional multilayer analytical element described for instance in the aforementioned Japanese Patent Provisional Publication No. 57(1982)-144996, an error is sometimes observed in the measurement due to the pyruvic acid contained in the liquid sample, i.e., intrinsic pyruvic acid.

SUMMARY OF THE INVENTION

It is an object of the present invention to provide a multilayer analytical element with which transaminase analysis can be performed without the complicated long procedure of the prior art while reducing error caused by the interference by the intrinsic pyruvic acid.

The above-described object is accomplished by a multilayer analytical element according to the invention, comprising at least a water-impermeable and light-transmissive support, a reagent layer and a porous spreading layer, superposed in this order, which is characterized in that said porous spreading layer has a void volume in the range of 3 to 15 $\mu l/cm^2$.

The void volume stated herein is a value obtained by multiplying the thickness of the porous spreading layer by a void ratio of the layer, and expressed by the void volume per a unit area of the porous spreading layer.

When the analytical element of the invention is employed, the color-forming reaction caused by the presence of the intrinsic pyruvic acid is terminated in an initial period in the measurement, so that the error caused by the interference of the intrinsic pyruvic acid is substantially reduced in the analysis.

DETAILED DESCRIPTION OF THE INVENTION

Examples of the water-impermeable and light-transmissive supports employable for the analytical element of the invention include known water-impermeable transparent supports in the form of a film prepared from materials, such as, polyethylene terephthalate, cellulose esters, (e.g., cellulose diacetate, cellulose triacetate and cellulose acetate propionate), polycarbonate and polymethyl methacrylate, or in the form of a plate, such as, a glass plate. The thickness of the support generally ranges from approx. 50 $\mu m$ to approx. 2 mm.

The above-described transparent support may contain a variety of pigments, such as, carbon black, titanium dioxide and copper phthalocyanine. Further, an opaque support, such as, a release paper can be employed in the invention. In the case of using the release paper as the support, the support is separated from the element after the analytical reaction terminates, and then the sequential measurement is done.

If necessary, the surface of the support can be provided with a subbing layer or an adhesive layer for enhancing the bonding strength between the support and the reagent layer or between the support and a water-absorbing layer optionally provided on the support.

The reagent layer employable in the present invention is a water-absorbing and water-impermeable layer in which a reagent composition containing pyruvic acid oxidase is substantially homogeneously dissolved or dispersed in a polymer binder, such as, gelatin or a mixture of gelatin and other hydrophilic polymer.

Examples of the gelatin employable for the reagent layer include alkali-treated gelatin, acid-treated gelatin, deionized gelatin and other gelatin derivatives. As the binder for the reagent layer, there can be employed a combination of gelatin and an appropriate amount of hydrophilic polymer which is miscible with gelatin. Examples of the hydrophilic polymer include agarose, pullulan, pullulan derivatives, polyacrylamide, polyvinyl alcohol and polyvinyl pyrrolidone as described in Japanese Patent Provisional Publications No. 59(1984)-171864 and No. 60(1985)-115859.

The reagent layer further contains an indicator for detecting hydrogen peroxide produced in the reaction caused by the above-mentioned pyruvic acid oxidase.

As a useful indicator for detecting hydrogen peroxide, there can be mentioned an indicator capable of producing a detectable change in the presence of peroxidase and hydrogen peroxide, or in the presence of a substance having the same function as that of peroxidase and hydrogen peroxide. The detectable change utilized in the invention is, for instance, color formation, color change or light emission.

Examples of the indicator for detecting hydrogen peroxide employable in the invention include those as described in Japanese Patent Provisional Publications. No. 49(1974)-53888, No. 51(1976)-40191, No. 53(1978)-131089 and No. 55(1980)-124499.

As the peroxidase or the substance having the same function as that of peroxidase, there can be mentioned peroxidase extracted from various organisms, synthetic peroxidase, and other chemical substances showing the same function as that of peroxidase which are extracted from organisms, as described in Japanese Patent Provisional Publication No. 50(1975)-137192. Preferred is peroxidase, and the peroxidase can be employed in the amount ranging from 0.3 U to 5 U, preferably from 0.5 U to 2 U, per 1 U of POP.

Examples of the color-forming indicator favorably employed in the invention include a Trinder reagent as described in Japanese Patent Publication No. 58 (1983)-28277 (column 2), an improved Trinder reagent indicator composition as described in Japanese Patent Provisional Publication No. 59(1984)-54962, and a leuco dye as described Japanese Patent Provisional Publications No. 53(1978)-26188 and No. 59(1984)-193352.

The thickness of the reagent layer generally ranges from approx. 3 $\mu m$ to approx. 50 $\mu m$, preferably from approx. 5 $\mu m$ to 30 $\mu m$, in the dry state. The (per area) amount of the reagent layer provided on the support generally ranges from approx. 3 $g/m^2$ to approx. 50 $g/m^2$ preferably from approx 5 $g/m^2$ to approx. 30 $g/m^2$. The reagent layer can contain various known additives, such as, a pH buffering agent, an organic carboxylic acid, an acid polymer and a basic polymer to adjust pH condition in the analytical operation. Into the reagent layer can be further incorporated other additives, such as, a mordant or a polymer mordant. The reagent layer preferably is transparent, but a small amount of titanium dioxide fine particles, barium sulfate fine particles or carbon black can be incorporated into the reagent layer for adjusting the optical property as desired.

There is no specific limitation on the pyruvic acid oxidase (hereinafter referred to as POP) employable in the invention, and any enzyme can be employed, provided that the enzyme serves as a catalyst for accelerating the reaction in which acetylphosphoric acid, carbon dioxide and hydrogen peroxide are produced from pyruvic acid, inorganic phosphoric acid and oxygen. Preferred is POP obtained by cultivation of bacteria belonging to Pediococcus genus, Streptococcus genus, or Aerococcus genus. Methods of gathering POP are described, for instance, in the aforementioned Japanese Patent Provisional Publication No. 55(1980)-13068. POP is commercially available, and it can be obtained easily. Pyruvic acid oxidase described in Japanese Patent Provisional Publication No. 59(1984)-162877 is also favorably employed in the present invention.

As a compound for supplying phosphoric acid (i.e., compound as a source of phosphoric acid), there can be employed phosphoric acid ion ($PO_4^{3-}$), phosphoric acid ion containing acidic hydrogen ($HPO_4^{2-}$, $H_2PO_4^-$), acids thereof, and salts thereof. Phosphoric acid esters or complexes capable of producing phosphoric acid ion or phosphoric acid ion containing acid hydrogen by the hydrolytic action can be also employed. Examples of the compound serving as the phosphoric acid source include phosphoric acid ($H_3PO_4$), trisodium phosphate, disodium hydrogen phosphate, sodium dihydrogen phosphate, tripotassium phosphate, dipotassium hydrogen phosphate, potassium dihydrogen phosphate, aluminum hydrogen phosphate, calcium hydrogen phosphate, manganese phosphate, manganese hydrogen phosphate, magnesium hydrogen phosphate, iron hydrogen phosphate, and cobalt hydrogen phosphate. The compound serving as the phosphoric acid source can be employed in the form of a buffering liquid of a phosphoric acid salt. These compounds may be incorporated into the reagent layer, as well as the spreading layer and other layers optionally provided between the reagent layer and the spreading layer (e.g., an adhesive layer and a light-blocking layer). The compound serving as the phosphoric acid source is generally employed in an amount ranging from 0.1 μmole to 10 μmoles, preferably 0.3 μmole to 5 μmoles per 1 U of POP based on the amount of phosphoric acid ion. As used herein, 1 U of POP means an activity capable of producing 1 μmole of hydrogen peroxide at 37° C. for one minute.

In the present invention, the reagent layer preferably contains pyruvic acid oxidase, and preferably contains other coenzyme. For instance, thiamine pyrophosphate (TPP) or flavine adenine dinucleotide (FAD) may be contained in the reagent layer.

Flavine adenine dinucleotide is generally employed in the amount of 0.-50 nmoles, preferably 0.3–30 nmoles, per 1 U of POP.

Examples of the thiamine pyrophosphates include thiamine diphosphoric acid (TDP) and thiamine triphosphoric acid (TTP). Preferred is thiamine triphosphoric acid. Thiamine pyrophosphate is generally employed in the amount of 5–500 nmoles, preferably 10–300 nmoles, per 1 U of POP.

These coenzymes may be incorporated into not only the reagent layer but also the spreading layer and other layers optionally provided between the reagent layer and the spreading layer (e.g., an adhesive layer and a light-blocking layer).

The activity of POP can be enhanced by further incorporating a divalent or trivalent metallic ion into the reagent layer in addition to POP. Examples of the metallic ion include $Ca^{2+}$, $Co^{2+}$, $Mg^{2+}$, $Mn^{2+}$ and $Al^{2+}$. These metallic ions can be incorporated in the form of a salt or a complex which contains the metallic ion and can release the metallic ion. In the case of using phosphate or hydrogen phosphate as a salt containing a divalent or trivalent metallic ion, there can be employed in the invention one compound containing the divalent or trivalent metallic ion and also serving as the aforementioned compound for supplying phosphoric acid. Examples of the salt containing a divalent or trivalent metallic ion include chloride, sulfate, nitrate, phosphate, hydrogen sulfate, hydrogen phosphate, carbonate, hydrogen carbonate, and acetate. Examples of the preferred metallic salt include manganese chloride (II), manganese phosphate (II), manganese hydrogen phosphate (II), magnesium chloride (II), and magnesium hydrogen phosphate (II). The metallic ion is generally employed in the amount of 5 nmoles to 200 μmoles, preferably 10 nmoles to 100 μmoles, per 1 U of POP.

There is no specific limitation on the material of the porous spreading layer, so long as the spreading layer has a void volume in the range of 3–15 μl/cm².

Examples of the material employable for the spreading layer include woven fabrics such as plain weave fabrics (e.g., broadcloth and poplin) as described in Japanese Patent Provisional Publications No. 55(1980)-164356 and No. 57(1982)-66359; knitted fabrics such as tricot knitted cloth, double knitted cloth and milanese knitted cloth as described in Japanese Patent Application No. 59(1984)-79158; processed papers containing organic polymer fibrous pulp as described in Japanese Patent Provisional Publication No. 57(1982)-148250; a non-fibrous, isotropic and porous material such as a membrane filter (made of brush polymer) or a porous material having continuous fine voids which comprises polymer microbeads, glass microbeads and diatomaceous earth preserved in a hydrophilic polymer binder as described in U.S. Pat. No. 3,992,158; and a non-fibrous, isotropic and porous material having continuous fine voids (a material having a three-dimensional lattice structure) comprising polymer microbeads adhering to each other in the state of point-contacting with a polymer adhesive which does not swell with water as described in Japanese Patent Provisional Publication No. 55(1980)-90859. Tricot knitted cloth or woven fabrics having been subjected to a calender treatment is preferably employed.

In the case of incorporating a reagent composition containing an enzyme into the porous spreading layer, preferred is a fibrous material such as a woven fabric or a knitted fabric from the viewpoint of easy preservation of the reagent composition in the layer.

The woven fabric or knitted fabric employable for the porous spreading layer is preferably subjected to a physical activation treatment such as a glow discharge treatment or a corona discharge treatment on one surface thereof to make the fabric hydrophilic so as to enhance the adhesion to an underlying layer (a layer nearer to the support), as described in Japanese Patent Provisional Publication No. 57(1982)-66359. For the same purpose, the fabric can be subjected to other processes such as a degreasing process comprising water washing and a hydrophilic polymer permeating process as described in Japanese Patent Provisional Publications No. 55(1980)-164356 and No. 57(1982)-66359. These processes can be employed by appropriately combining with each other.

Between the reagent layer and the spreading layer can be provided a light-blocking layer or a light-reflecting layer. The light-blocking layer or the light-reflecting layer has light-blocking and/or light-reflecting properties, and comprises a hydrophilic polymer binder and white fine particles of titanium dioxide, barium sulfate, etc. dispersed therein. The thickness of the light-blocking layer or the light-reflecting layer is generally in the range of approx. 2–20 μm in dry state.

Further, an adhesive layer made of a hydrophilic polymer such as gelatin can be provided on the surface of the reagent layer (or the surface of the light-blocking layer or light-reflecting layer in the case that such layer is provided) to enhance the adhesion to the spreading layer for integration. The thickness of the adhesive layer is generally in the range of approx. 0.5–5 µm in dry state.

The porous spreading layer can contain various substrates depending upon the analyte of the analysis. For instance, in the measurement of alanine transferase (ALT) activity, L-alanine and α-ketoglutaric acid are incorporated into the spreading layer in combination with an appropriate buffering agent. Likewise, in the measurement of each activity of aspattic acid aminotransferase (AST), lactate dehydrogenase (LDH), glycerophosphokinase (GK), creatinine phosphokinase (CK), and myokinase, a substrate corresponding to each enzyme is incorporated into the spreading layer in combination with each conjugated enzyme.

These substrates and conjugated enzymes are described in Japanese Patent Provisional Publication No. 55(1980)-13068. The substrate, conjugated enzyme and buffering agent may be incorporated into not only the spreading layer but also the reagent layer or other additional layers provided between the spreading layer and the reagent layer.

The spreading layer may further contain other materials such as a hydrophilic polymer, a surfactant, a light-blocking composition (e.g., a dispersion of titanium dioxide), and a divalent or trivalent metallic salt. serving as a POP activator.

It is said that the pH value suitable for the activation of pyruvic acid oxidase is in the range of approx. 6.5–8.0.

In the present invention, the reagent layer and/or other layers (e.g., spreading layer and other additional layers provided-between the spreading layer and the reagent layer such as an adhesive layer or a light-blocking layer) may contain a buffering agent to accomplish the suitable pH for maintaining the activation of pyruvic acid oxidase. Examples of the buffering agents include compositions corresponding to a phosphoric acid buffering agent, tris-hydrochloric acid buffering agent, Good's buffering agent, etc.

The reagent layer according to the present invention may be in the form of a single layer or may be composed of two or more layers. When the reagent layer is composed of two or more layers, it is possible that one layer contains pyruvic acid oxidase (and other additives such as an coenzymes thereof, an activator and a source of phosphoric acid, if necessary), and one of the other layers contains a reagent for detecting hydrogen peroxide (generally containing peroxidase).

The above-described reagent layer, light-blocking layer, light-reflecting layer, adhesive layer and spreading layer may contain a surfactant such as a nonionic surfactant. Examples of the nonionic surfactants include p-octylphenoxypolyethoxyethanol, p-nonylphenoxypolyethoxyethanol, polyoxyethylene oleyl ether, polyoxyethylene sorbitan monolaurate, p-nonylphenoxypolyglycydol, and octylglucoside. The spreading effect (i.e., metering effect) of an aqueous liquid sample is substantially improved by incorporating the nonionic surfactant into the spreading layer. The incorporation of the nonionic surfactant into the reagent layer makes it possible that water in the aqueous liquid sample is substantially homogeneously absorbed in the reagent layer during the analytical operation, and that the water is rapidly and homogeneously brought into contact with the spreading layer.

When the activities of various transaminases contained in body fluids having a relatively high concentration of intrinsic pyruvic acid, particularly in blood, are measured by a method utilizing reaction rate by using the integral multilayer analytical element according to the present invention, the enzyme activity can be measured without any measuring error caused by intrinsic pyruvic acid even if the reaction time is relatively short.

The following examples and comparison examples are given to further illustrate the present invention, but the examples by no means restrict the invention.

EXAMPLE 1

On the surface of a colorless transparent polyethylene terephthalate (PET) film having a thickness of 180 µm (provided with an undercoated layer of gelatin) was applied a coating solution having the following composition in the amount of 150 cc/m² and dried to form a reagent layer having a thickness of approx. 15 µm in dry state for measuring the activity of alanine aminotransferase (ALT).

| Coating Solution for Reagent Layer | |
|---|---|
| Gelatin | 20 g./m² |
| Surfactant 10G | 0.8 g./m² |
| (available from Oline Corp.) | |
| Peroxidase | 1,500 U/m² |
| FAD | 24 mg./m² |
| TPP | 100 mg./m² |
| Pyruvic acid oxidase | 15,000 U/m² |
| Leuco dye | 300 mg./m² |

The above-listed leuco dye had the following formula:

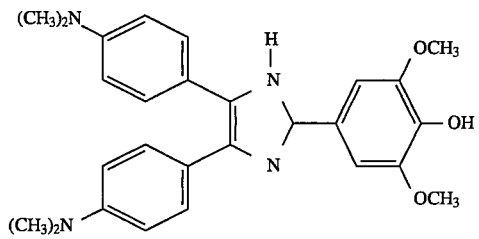

On the reagent layer prepared as above a coating solution having the following composition in the amount of 60 cc/cm² was applied and dried, to form an adhesive layer having a thickness of 3 µm in dry state.

| Coating Solution for Adhesive Layer | |
|---|---|
| Gelatin | 4 g./m² |
| Surfactant 10G | 0.16 g./m² |

The surface of the adhesive layer was wetted with water in the amount of approx. 30 g/m². A broadcloth made of polyester (void volume: 9.8 µl/cm²) was laminated onto the wetted surface of the adhesive layer under light pressure and dried, to form a spreading layer.

The spreading layer was homogeneously incorporated with an aqueous solution of a reagent having the following composition in the amount of 100 cc/m² and dried, to prepare a multilayer analytical element for the measurement of ALT activity.

| Composition of Reagent Solution | |
|---|---|
| Tris(hydroxymethyl)aminoethane | 0.22 g./m² |

-continued

| Composition of Reagent Solution | |
|---|---|
| Potassium phosphate | 0.45 g./m² |
| α-Ketoglutaric acid | 0.4 g./m² |
| Metholose 90SH100 | 0.87 g./m² |
| (available from Shinetsu Chemical Co., Ltd.) | |
| Titanium dioxide (rutile type) | 7 g./m² |
| L-Alanine | 3 g./m² |
| Magnesium chloride | 0.24 g./m² |
| Ascorbic acid oxidase | 18,000 U/m² |

COMPARISON EXAMPLE 1

The procedure of Example 1 was repeated except that a tricot fabric made of polyester (void volume: 20 µl/cm²) instead of the broadcloth, to prepare a multi-layer analytical element for the measurement of ALT activity for comparison.

On each of the spreading layers of the multilayer analytical elements for measuring the ALT activity prepared in Example 1 and Comparison Example 1 was spotted 10 µl of 7% HSA (human serum albumin) containing pyruvic acid in the amounts set forth in Table 1. The element spotted with HSA was placed in a sealed container, and the temperature within the container was kept at 37° C. Then, the time required for the coloring of the reagent layer by the action of pyruvic acid at a maximum level was measured. The results are set forth in Table 1.

TABLE 1

| Amount of pyruvic acid (µM) | 100 | 200 | 500 | 1,000 |
|---|---|---|---|---|
| Example 1 | 40 sec. | 100 sec. | 2 min. | 2 min. |
| Com. Example 1 | 8 min. | 8 min. | 8 min. | 10 min. |

As is evident from the results set forth in Table 1, in a multilayer analytical element of the present invention, the pyruvic acid in the HSA sample is very rapidly consumed. In other words, it was confirmed that the element of the present invention was hardly affected by the presence of the intrinsic pyruvic acid.

Subsequently, on each of the spreading layers of the multilayer analytical elements for measuring the ALT activity prepared in Example 1 and Comparison Example 1 was spotted 10 µl of four kinds of control serums (ALT activity: 52 U/l) having the different amounts of pyruvic acid set forth in Table 2. The element spotted with the control serum was placed in a sealed container, and then the color of the reagent layer of the element was measured at an interval of 20 seconds by photometry utilizing a reflected light while keeping the temperature in the container at 37° C. The values measured between 2 minutes and 3 minutes after the measurement was started was applied to a calibration curve (previously determined) to determine the ALT activity. The results are set forth in Table 2. The values of Example 1 and Comparison Example 1 set forth in Table 2 are the measured values of ALT activity (U/l).

TABLE 2

| Amount of pyruvic acid in control serum (µM) | 0 | 100 | 200 | 500 |
|---|---|---|---|---|
| Example 1 | 52 | 52 | 51 | 51 |
| Com. Example 1 | 50 | 52 | 58 | 69 |

As is evident from the results set forth in Table 2, the ALT activity was obtained with positive errors caused by the intrinsic pyruvic acid in the measurement using the analytical element of Comparison Example 1. In contrast, no error was obtained in the measurement of ALT activity using the analytical element of Example 1 according to the present invention even when a large amount of intrinsic pyruvic acid, namely 500 µM, was contained in the sample.

EXAMPLE 2

The procedure of Example 1 was repeated except that L-alanine was replaced With aspartic acid and oxaloacetic acid was permeated decarboxylase in the amount of 15,000 U/m² was permeated in the porous spreading layer, to prepare a multi-layer analytical element for the measurement of aspartic acid aminotransferase (AST) activity.

COMPARISON EXAMPLE 2

The procedure of Example 2 was repeated except for using a tricot fabric made of polyester fiber (void volume: 20 µl/cm²) as a porous spreading layer, to prepare a multilayer analytical element for the measurement of AST activity.

On each of the spreading layers of the multilayer analytical elements prepared in Example 2 and Comparison Example 2 was spotted 10 µl of four kinds of control serums (AST activity: 72 U/l) having the different amounts of pyruvic acid set forth in Table 3. The element spotted with the control serum was placed in a sealed container, and the color of the reagent layer of the element was measured at an interval of 10 seconds by photometry utilizing a reflected light under keeping the temperature in the container at 37° C. The values measured between 2 minutes and 3 minutes after the measurement was started was applied to the calibration curve to determine the AST activity. The results are set forth in Table 3.

TABLE 3

| Control serum | a | b | c | d |
|---|---|---|---|---|
| Amount of pyruvic acid (µM) | 0 | 100 | 200 | 500 |
| AST activity (U/l) | | | | |
| Example 2 | 72 | 72 | 71 | 73 |
| Com. Example 2 | 72 | 75 | 85 | 91 |

As is evident from the results set forth in Table 3, the AST activity was obtained with positive errors caused by the intrinsic pyruvic acid in the measurement using the analytical element of Comparison Example 2. In contrast, no error was obtained in the measurement of ALT activity using the analytical element of Example 2 according to the present invention even when a large amount of intrinsic pyruvic acid, namely 500 µM, was contained in the sample.

We claim:

1. A method for quantitatively measuring alanine aminotransferase in a liquid sample selected from the group consisting of serum, plasma and whole blood, said liquid sample containing intrinsic pyruvic acid in an amount of not less than 2 mg/dl which comprises the steps of: spotting the liquid sample onto a multilayer analytical element comprising a water-impermeable and light-transmissive support, a reagent layer arranged on the support and a porous spreading layer arranged on the reagent layer, said reagent layer containing pyruvic acid oxidase, peroxidase, and a reagent composition which produces a colored substance by the action of hydrogen peroxide in the presence of peroxidase, said spreading layer having a void volume in the range of 3–15 $\mu l/cm^2$, and said reagent layer or said spreading layer containing an alpha-ketoglutaric acid and L-alanine; incubating the multilayer analytical element on which the liquid sample has been spotted to produce the colored substance; and photometrically measuring the colored substance in the analytical element.

2. The method of claim 1, wherein said spreading layer is a polyester broadcloth.

3. The method of claim 1, wherein said spreading layer further contains a divalent or trivalent metallic ion.

4. The method of claim 1 wherein said spreading layer further contains a light-blocking composition.

5. The method of claim 1 wherein said reagent composition contains a leuco dye.

6. A method for quantitatively measuring aspartic acid aminotransferase in a liquid sample selected from the group consisting of serum, plasma and whole blood, said liquid sample containing intrinsic pyruvic acid in an amount of not less than 2 mg/dl which comprises the steps of: spotting the liquid sample onto a multilayer analytical element comprising a water-impermeable and light-transmissive support, a reagent layer arranged on the support and a porous spreading layer arranged on the reagent layer, said reagent layer containing pyruvic acid oxidase, peroxidase, and a reagent composition which produces a colored substance by the action of hydrogen peroxide in the presence of peroxidase, said spreading layer having a void volume in the range of 3–15 $\mu l/cm^2$, and said reagent layer or said spreading layer containing an alpha-ketoglutaric acid, L-aspartic acid, and oxaloacetic acid decarboxylate; incubating the multilayer analytical element on which the liquid sample has been spotted to produce the colored substance; and photometrically measuring the colored substance in the analytical element.

7. The method of claim 6 wherein said spreading layer is a polyester broadcloth.

8. The method of claim 6 wherein said spreading layer further contains a divalent or trivalent metallic ion.

9. The method of claim 6 wherein said spreading layer further contains a light-blocking composition.

10. The method of claim 6 wherein said reagent composition contains a leuco dye.

* * * * *